(12) United States Patent
Reinbold

(10) Patent No.: US 7,877,832 B2
(45) Date of Patent: Feb. 1, 2011

(54) TOOTHBRUSH

(75) Inventor: Klaus Reinbold, Buehl (DE)

(73) Assignee: GlaxoSmithKline Consumer Healthcare GmbH & Co. KG, Buhl (DE)

( * ) Notice: Subject to any disclaimer, the term of this patent is extended or adjusted under 35 U.S.C. 154(b) by 799 days.

(21) Appl. No.: 10/583,843

(22) PCT Filed: Dec. 20, 2004

(86) PCT No.: PCT/EP2004/014579

§ 371 (c)(1),
(2), (4) Date: Sep. 24, 2007

(87) PCT Pub. No.: WO2005/060866

PCT Pub. Date: Jul. 7, 2005

(65) Prior Publication Data

US 2008/0120795 A1 May 29, 2008

(30) Foreign Application Priority Data

Dec. 22, 2003 (GB) .................................. 0329678.7

(51) Int. Cl.
*A61C 17/22* (2006.01)
(52) U.S. Cl. .............................. 15/22.1; 15/22.2; 15/28
(58) Field of Classification Search .................. 15/22.1, 15/22.2, 22.3, 22.4, 23, 28
See application file for complete search history.

(56) References Cited

U.S. PATENT DOCUMENTS

| 3,939,599 | A | * | 2/1976 | Henry et al. ................... 433/99 |
| 4,450,599 | A | * | 5/1984 | Scheller et al. ............... 15/22.1 |
| 2002/0124333 | A1 | | 9/2002 | Hafliger et al. ............... 15/22.1 |

FOREIGN PATENT DOCUMENTS

| EP | 481553 | * | 4/1992 |
| EP | 0 628 291 | A2 | 12/1994 |
| GB | 2 097 663 | A | 11/1982 |
| WO | WO 92/10979 | | 7/1992 |
| WO | 98/01083 | * | 1/1998 |

* cited by examiner

*Primary Examiner*—Mark Spisich
(74) *Attorney, Agent, or Firm*—Joshua C. Sanders; Theodore R. Furman

(57) ABSTRACT

An electrically powered toothbrush comprising a handle which contains an electric motor and power supply, a head part connected to the handle to be driven in motion by the electric motor by a transmission means between the motor and the oral head part. The head part is flexibly and resiliently connected to the handle such that the head part can move resiliently under pressure of the oral hygiene part against a tooth surface. The motor is moveably mounted within the handle and the assembly of motor and transmission means is pivotally connected to the handle at a pivot point between the brush head and the motor. Suitably the handle is in two parts with a flexible connection between the parts.

13 Claims, 3 Drawing Sheets

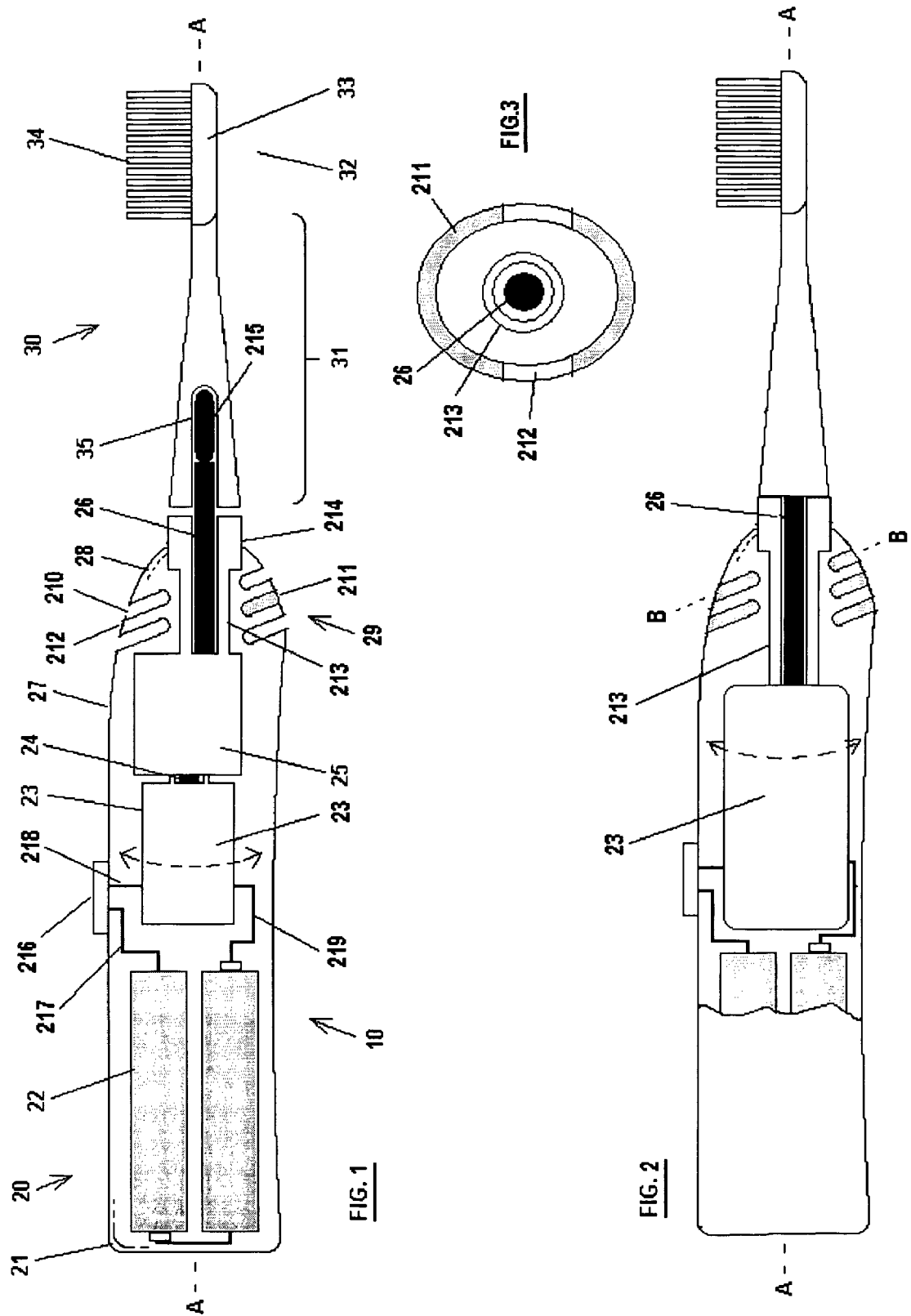

TOOTHBRUSH

This invention relates to toothbrushes, in particular to electrically powered toothbrushes.

Electrically powered toothbrushes generally comprise a handle which contains inter alia a power supply and a drive motor, and a head part connected to the handle and which incorporates a brush head which supports one or more oral hygiene part to be driven by the motor. The handle and brush head are normally disposed along a longitudinal toothbrush direction. Often the head part comprises a neck part between the brush head and the handle. Generally the handle also includes a transmission means such as a drive shaft between the motor and the brush head, with optionally a gear system between the motor and the drive shaft by means of which rotary or other motion from the motor is transmitted to the brush head to thereby move the oral hygiene part in a suitable oral hygiene motion.

Numerous types of oral hygiene motion are known. For example the brush head may be moved in rotary motion about a rotation axis transverse to the handle-brush head direction, which may be oscillatory rotary, i.e. motion involving reciprocal angular displacement about a mean position. Suitable means for achieving such oscillatory motion are well known in commercially available electric toothbrushes. For example a rotary motor may be caused, e.g. by suitable electronic control, to output oscillatory rotary motion through a small angle e.g. ca.+/−10° at a suitable frequency e.g. ca. 500 Hz. Sometimes the rotary motion also involves a reciprocal back and forth movement of the oral hygiene part along the rotational axis direction. EP-A-0 628 291 discloses a motion with two superimposed movements, and in which a drive shaft connects the brush head to the motor. Another known type of oral hygiene motion is a so called "Bass" motion, i.e. motion according to the known Bass technique, in which the oral hygiene part is moved both reciprocally longitudinally and also in oscillatory rotation about a rotation axis generally parallel to the longitudinal direction. Motion of this latter type is for example disclosed in EP-A-0 628 291, WO 93/09729, and U.S. Pat. No. 3,577,579 which also discloses suitable transmission means to convert rotary motion from the motor into such oral hygiene motion. Another type of motion is one in which the motor causes the brush head to vibrate at a suitable frequency. Motion of this kind is for example disclosed in EP-A-0 850 602, in which a rotary motor rotates a drive shaft carrying an eccentric weight.

Often the head part or brush head is replaceable. For example the brush head may be replaceably connectable to the end of the head part remote from the handle. Alternatively the brush head may be integral with the neck, and the neck may be replaceably connectable to the handle at the end of the head part remote from the brush head.

The term "oral hygiene part" as used herein refers to a part which contributes to oral hygiene, for example by cleaning the teeth, gums or other oral tissues, and/or polishing or whitening the teeth, and/or massaging the gums or other oral tissues. Numerous types of oral hygiene part are known. Bristles, generally arranged in tufts, are the most common type of oral hygiene part but other types are known.

A problem with all toothbrushes, including electrically powered toothbrushes, is that of alleviating excessive pressure of the oral hygiene part against the teeth or other oral tissues. Another problem is that of enabling the brush head to adapt its position to the shape of the teeth so as to reach all tooth surfaces for cleaning. A solution to these problems in electric powered toothbrushes is offered by flexible linking between for example the brush head and neck as in EP-A-1 182 254 in which the brush head is connected to the neck part by a resiliently flexible link. An alternative solution is for example provided by WO-A-94/05299 and U.S. Pat. No. 5,406,664 in which the neck is flexibly linked to the handle. Both of these solutions require a complex transmission means between the motor and the oral hygiene part, e.g. a flexible link in the transmission means, because the transmission means needs to be flexible in a direction transverse to the longitudinal axis. GB-A-2 097 663 and EP-A-0 481 553 both disclose electric toothbrushes in which the motor is mounted on a pivot so as to be able to pivot about a single pivot axis transverse to the longitudinal direction, and a spring is located between the motor and the inside surface of the handle.

It is an object of this invention to provide an improved electrically powered toothbrush with flexible linking between the brush head and handle with a simplified transmission means.

According to this invention an electrically powered toothbrush is provided comprising:

a handle which contains an electric motor and an electrical power supply, a head part connected to the handle and incorporating an oral hygiene part to be driven in motion by the electric motor, a transmission means between the motor and the oral hygiene part the head part being flexibly and resiliently connected to the handle such that the head part can move resiliently under pressure of the oral hygiene part against a tooth surface, the motor being moveably mounted within the handle, and the head part and motor are connected together such that said movement of the head part under the pressure of the oral hygiene part against a tooth surface is communicated to the motor to cause the motor to move in response to said movement, characterised in that:

the assembly of motor and transmission means is pivotally connected to the handle at a pivot point between the brush head and the motor.

By the construction provided by the invention a simpler transmission means can be achieved because under pressure of the oral hygiene part against a tooth surface the motor and the head part move together, so they do not need to be connected by a transmission means that is flexible to accommodate relative motion of the head part and the motor. That is, the position and connection of the motor and head part relative to each other may be rigid.

The handle may typically comprise a plastics material shell enclosing its internal components e.g. the motor and batteries, as common in the art. Typically the handle is elongate along the toothbrush longitudinal direction to facilitate grip by the user having an end closest to the head part and an opposite end remote from the head part.

The transmission means may also be moveably mounted within the handle so that the movement of the head part under the pressure of the oral hygiene part against a tooth surface is communicated to the transmission means to move in response to said movement. For example the motor and transmission means may be rigidly connected so that they move in this way together. That is, the position of the motor and transmission means relative to each other may be rigid. For example the motor may be rigidly connected to a gear system and a sleeve supporting the drive shaft by means of a motor housing which is integrally extended to also house the gear system and to form such a sleeve.

The transmission means typically comprises a drive shaft between the motor and the oral hygiene part to transmit motion to the oral hygiene part. The transmission means may optionally comprise a gear box between the motor and the drive shaft. Such a gear system may be generally conventional, comprising for example a reduction gear system to reduce or increase the speed of rotation transmitted from the motor to the shaft, and/or means to convert rotary motion to another mode of motion of the drive shaft. The gear system may for example include conventional gearbox components such as intermeshing gear wheels etc.

The transmission means may transmit any of the above-mentioned types of motion to the oral hygiene part. The transmission means may for example transmit rotary motion to the brush head to drive the brush head in rotary oral hygiene motion. Such rotary motion may be oscillatory rotary motion. The transmission means may for example transmit motion to the brush head to drive the brush head in the so called "Bass" motion in which the oral hygiene part is moved both reciprocally longitudinally in the head part—handle direction, i.e. in the elongate direction of the drive shaft, and also in oscillatory rotation about a rotation axis generally parallel to the longitudinal direction, i.e. the longitudinal axis of the drive shaft. Such a gear system is for example disclosed in above-mentioned EP-A-0 628 291 and U.S. Pat. No. 3,577,579.

The drive shaft may be generally conventional, comprising for example a metal or rigid plastics material shaft connected to an output shaft of the motor or of the gear system and being connected or connectable to the oral hygiene part.

The gear system if present in such a transmission means may be located within the handle. Normally the gear system will be enclosed within a gear housing.

The assembly of motor and transmission means is pivotally connected to the handle at a pivot point between the brush head and the motor, for example at a pivot point located along the drive shaft between the motor and the brush head, or if a gear system is present, preferably between the gear system and the brush head, for example at a pivot point located along the drive shaft between the gear system and the brush head. The assembly of motor, transmission means and head part can move pivotally about such a pivot point in response to movement of the head part under the pressure of the oral hygiene part against a tooth surface.

Such a pivot point may allow the head part to move pivotally within the envelope of a cone with its apex at the pivot point, or about an arc centred on the pivot point.

In an embodiment such a pivot connection may be provided by a handle which has a resiliently flexible section, and the transmission means passes through this resiliently flexible section. Such a resiliently flexible section may comprise a handle in two longitudinally disposed parts; a first part relatively further from the brush head, and a second part relatively closer to the brush head, a drive shaft passing through the first part of the handle in a direction toward the brush head, with a resiliently flexible connection between the first and second parts.

Such a resiliently flexible connection may be provided by an elastomer material section between the first and second parts. For example such an elastomer material section may be provided by means of a composite plastics material-elastomer material section between the first and second part. Such a composite region may for example comprise a plastics material section between the first and second parts incorporating one or preferably plural apertures in the plastics material which contain the elastomer material. Such one or preferably plural apertures may for example be in the form of elongate slots elongated in a direction transverse to the longitudinal direction.

Generally the handle will comprise a shell made of a plastics material and enclosing the internal components of the handle. In such a shell the above-mentioned elastomer material section between the first and second parts of the handle may be provided by a one or preferably plural apertures in the plastics material of the shell which contain the elastomer material. Such a shell can be made by known processes of injection moulding in which firstly the plastics material parts of the shell incorporating such aperture(s) is made, then a thermoplastic elastomer material is injected into the aperture(s).

For example the transmission means may comprise a sleeve having a bore through which the drive shaft passes, and the drive shaft may pass through the resiliently flexible section, e.g. through the above-mentioned first part of the handle, e.g. the shell via such a sleeve. Such a sleeve may be rigidly connected to the first part of the shell. For example such a sleeve may be a separate member rigidly connected to the first part of the shell, or may for example be integrally made with the first part of the shell.

The drive shaft may for example comprise a stub shaft extending from the end of the handle closest to the brush head, and to which a replaceable head part may be connected. Such stub shafts are well known. When the head part is replaceably connectable to the handle the drive shaft may pass through the wall of the first part of the shell, e.g. via such a sleeve, so that an end of the stub drive shaft projects outside of the wall of the handle, and this end may be connectable to the head part so as to thereby communicate motion to the head part.

For example if the brush head is to move with the above-mentioned Bass motion the entire head part may be moved when the head part is connected to the handle. Alternatively if the brush head is to be moved with rotary motion the head part may include a drive shaft extending longitudinally through the head part and which transmits rotary motion to the brush head. The sleeve may carry the shaft through the wall of the handle via a bush bearing.

The motor or the assembly of motor and transmission means may be unsupported within the handle except at the point at which the drive shaft passes through the shell, for example via such an above-mentioned sleeve, so that the motor or assembly is free to move within the handle as the motor or assembly and the head part pivot.

Alternatively the handle and motor or assembly may be provided with guide features to allow the motor or assembly to move within the handle only in preferred directions, and/or may be provided with abutment features to allow the motor or assembly to move within the handle only within defined limits, for example in an arc. Normally the oral hygiene part has a surface on which are mounted oral hygiene elements such as bristles and such an arc is preferably in a plane perpendicular to this surface.

According to another aspect of this invention a handle for an electrically powered toothbrush is provided comprising:

a handle which contains an electric motor and an electrical power supply, and is attachable to a head part, a transmission means between the motor and the oral hygiene part the head part being flexibly and resiliently connected to the handle such that the head part can move resiliently under pressure of the oral hygiene part against a tooth surface, the motor being moveably mounted within the handle, and the head part and motor are connected together such that said movement of the head part under the pressure of the oral hygiene part against a tooth surface is communicated to the motor to cause the motor to move in response to said movement, characterised in that:

the assembly of motor and transmission means is pivotally connected to the handle at a pivot point between the brush head and the motor.

Suitable and preferred features of such a handle are as discussed above.

In a particularly suitable form the assembly of motor and transmission means is pivotally connected to the handle at a pivot point between the brush head and the motor, for example at a pivot point located along the drive shaft between the motor and the brush head, or if a gear system is present, preferably between the gear system and the brush head, for example at a pivot point located along the drive shaft between the gear system and the brush head. The assembly of motor, transmission means and head part can move pivotally about such a pivot point in response to movement of the head part under the pressure of the oral hygiene part against a tooth surface.

The handle and head part may be otherwise generally conventional, for example made of the plastics materials, or plastics materials and elastomeric materials, metals etc. of which electrically powered toothbrushes are normally made.

The motor and transmission means may also be generally conventional. Typical electric motors commonly used in electric toothbrushes are rotary motors with an 0.3 W drive shaft power rating. The electric power supply and associated switching means may also be conventional, for example one or more replaceable and/or rechargeable battery cell. The electrical connections between the motor and electrical power supply and the switching means should be adaptable to the above-described movement of the motor, e.g. they may comprise flexible connectors such as wires, or connectors which slide over each other.

The oral hygiene part of the brush head may for example comprise generally conventional bristles, cleaning/polishing pads, elastomeric lamellae etc.

The invention will now be described by way of non-limiting example only, with reference to the accompanying drawings which show:

FIGS. 1 and 2 show schematic overall longitudinal sectional views of electric toothbrushes of this invention.

FIG. 3 shows a cross section through the handle of the toothbrushes of FIGS. 1 and 2

Figures 4, 5:
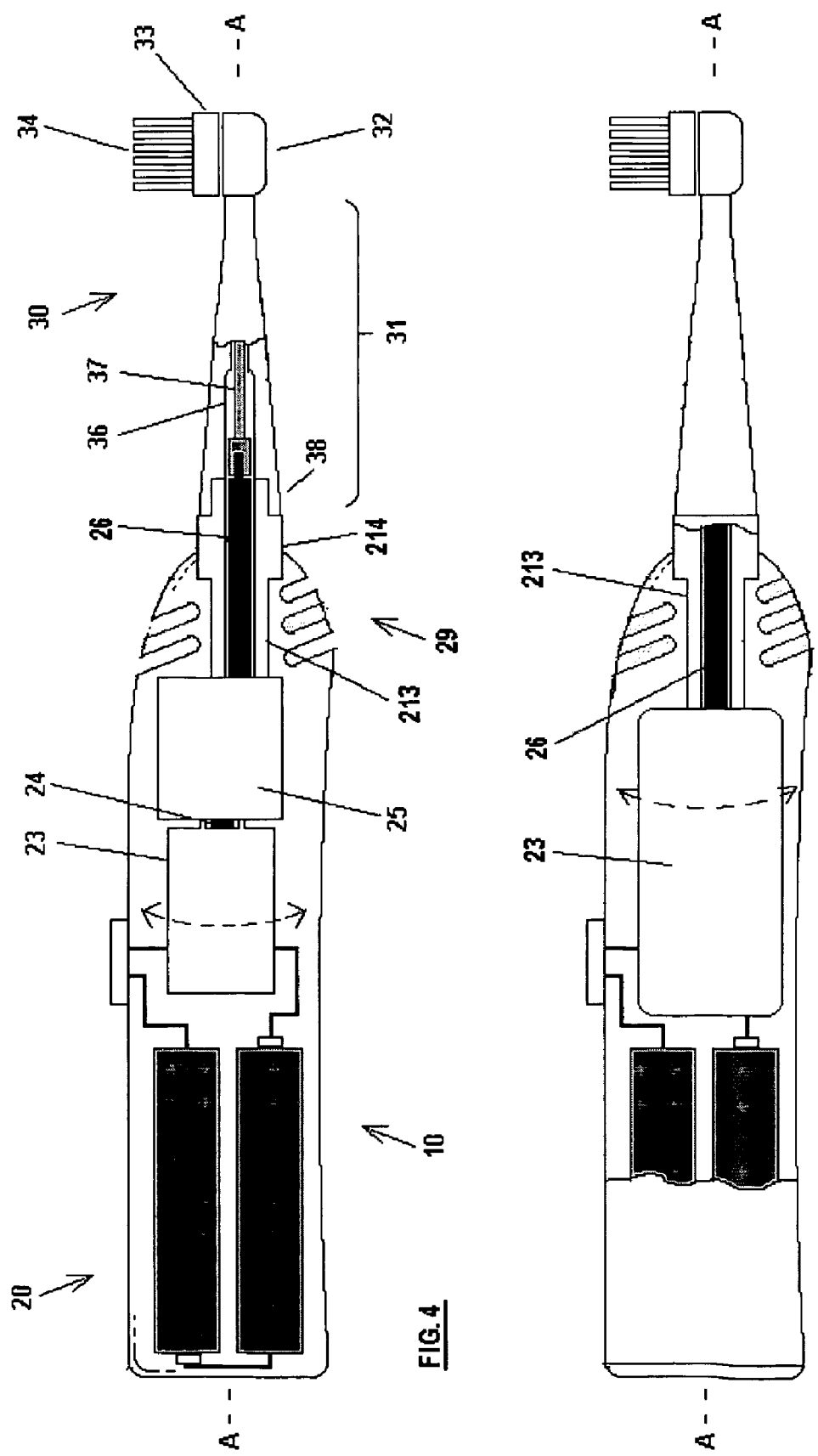
FIGS. 4 and 5 show schematic overall longitudinal sectional views of electric toothbrushes of this invention.

Referring to FIG. 1 an electric toothbrush is shown overall 10 in side view. The toothbrush 10 comprises an elongate hollow grip handle 20 bounded by a shell wall 21 (part shown) made of plastics material, at one end of the handle being connected a head part 30. The head part 30 comprises a neck 31 and a brush head 32. The brush head 32 comprises a support 33 in which bristles 34 are mounted and project in a bristle direction B. The bristle configuration shown is purely representative. The handle 20 and head part 30 lie along a handle-brush head direction (A-A) shown to be a straight line but which may enclose a non 180° angle or curve.

The handle 20 encloses a power supply comprising plural (two are shown, there may be more or less) conventional AA replaceable or rechargeable batteries 22, conventionally enclosed and conventionally supported in handle 20. If the batteries 22 are replaceable then handle 20 may be openable in a conventional manner, e.g. by the end of the handle 20 furthest from the head part 30 being removeable to facilitate replacement. Alternatively batteries 22 may be conventionally rechargeable.

Handle 20 also contains a conventional drive motor 23 typical of those used in conventional electric toothbrushes. Motor 23 drives its output shaft 24 in rotary motion about a rotation axis generally parallel to direction A-A at ca. 5000 rpm. Output shaft 24 is connected to gear system 25 enclosed conventionally in a gear casing, and converts the rotary motion of output shaft 24 into motion of a known type in which the output drive shaft 26 of gear system 25 moves longitudinally reciprocally in the direction A-A with a displacement ca. 1 mm and simultaneously in reciprocal oscillatory rotary motion about a rotation axis generally parallel to direction A-A with an amplitude ca 5-7°.

The handle shell 21 is made in two longitudinally disposed parts. There is a first part 27 relatively further from the brush head, and a second part 28 relatively closer to the brush head. Between parts 27 and 28 is a composite plastics material-elastomer material section 29 (generally). Composite region 29 comprises plural apertures 210 in the plastics material of shell 21 which contain an elastomer material 211, for clarity in FIG. 1 only one aperture 210 is shown containing elastomer 211. The plural apertures 210 are each in the form of slots elongated in a direction transverse to the longitudinal direction A-A. FIG. 3 shows the section 29 in a cross section as cut through line B-B of FIG. 2, and shows the plastics material bridging parts 212 between apertures 210. Such a structure can be produced using well known two-component injection moulding techniques as used currently in making electric toothbrush handles.

Drive shaft 26 passes through the second part 28 of shell 21 in a direction toward the brush head. Drive shaft 26 passes through a sleeve 213 which extends from gear system 25 and is rigidly connected to the wall of the second part 28 of the shell. This rigid connection may for example be by integral manufacture of the wall 21 and sleeve 213, or by means of a suitable bush bearing 214 rigidly mounted in an opening in wall 21. The part of drive shaft 26 outside of handle 20 is formed into stub axle 215.

The section 29 is resiliently flexible, and so causes the assembly of motor 23 and transmission means 25,26 to be pivotally connected to the shell 21 of handle 20 at a pivot point between the brush head 30 and the motor 23 at a pivot point located along the drive shaft 26 between the gear system 25 and the brush head 30, i.e. the point at which sleeve 213 is connected to second part 28 by bush 214. The assembly 23,25,26 can move pivotally about such a pivot point in response to movement of the head part 30 under the pressure of its oral hygiene part against a tooth surface.

Stub axle 215 is connectable e.g. by a known bayonet connection into a socket 35 in the end of head part 30 closest to handle 20. Shaft 26 and sleeve 213 may be made of low friction materials so that the head part 30 can be moved with the longitudinally reciprocally and reciprocal oscillatory rotary motion of shaft 26 within sleeve 213. For example shaft 26 may be made of smooth metal and sleeve 213 of smooth plastic, or plastic with a low friction sleeve lining. Motor 23, gear system 25 and sleeve 213 are rigidly connected together so that components 23, 25 and 26 are rigid against relative motion.

In use the motor 23 is actuated by operating the on-off switch 216 to connect motor 23 to batteries 22 via connectors 217,218,219 which are flexible, e.g. wires. This causes motor 23 to drive head part 30 via gear system 25 and shaft 26. There is a small gap between the longitudinally opposed facing surfaces of bush 214 and neck 31 to allow the longitudinal reciprocal motion of the head part 30.

When brush head 32 is pressed against the user's teeth (not shown) this causes the assembly of head part 30, sleeve 213, gear system 25 and motor 23 to pivot resiliently about bush 214 as the flexible region 29 resiliently deforms in response to this pressure, so that motor 23 moves within handle 20 in the arc shown and thereby reduce excessive brushing pressures on the teeth.

FIG. 2 shows an analogous construction in which motor 23 is connected directly to drive shaft 26 passing through sleeve 213 without an intermediate gearbox. In FIG. 2 all of the apertures 210 are shown containing elastomer 211.

FIGS. 4 and 5 show an alternative construction of toothbrush 10, parts corresponding to analogous parts in FIGS. 1 and 2 not being numbered for clarity. In FIGS. 4 and 5 head part 32 incorporates a rotatable support 33 for the bristles 34, mounted to rotate about a rotation axis perpendicular to A-A. Neck part 31 is a hollow shaft having an internal bore 36 along which passes a drive shaft 37, which is configured to drive support 33 in oscillatory rotary motion in a known manner. Neck part 31 replaceably connects to bush 214 at known bayonet connection 38, such that shafts 26 and 37 connect in a known way so that rotary motion of shaft 26 is communicated to shaft 37. In the construction of FIG. 4 the gear system 25 is such as to communicate rotary motion from motor 23 to shaft 26, and may include a gear so that shaft 26 rotates at a different speed than motor output shaft 24. The pivotal movement of the assembly 23,25,26,213 in the arc shown is analogous to that of FIGS. 1 and 2. FIG. 5 shows an analogous construction in which motor 23 is connected directly to drive shaft 26 passing through sleeve 213, without an intermediate gearbox. The embodiment of FIG. 5 is suitable for a brush head motion in which the motor is operated by electronic control of a known type which causes the motor 23 to rotate the shaft 26 with oscillatory rotary motion with a suitable frequency.

Figure 6:
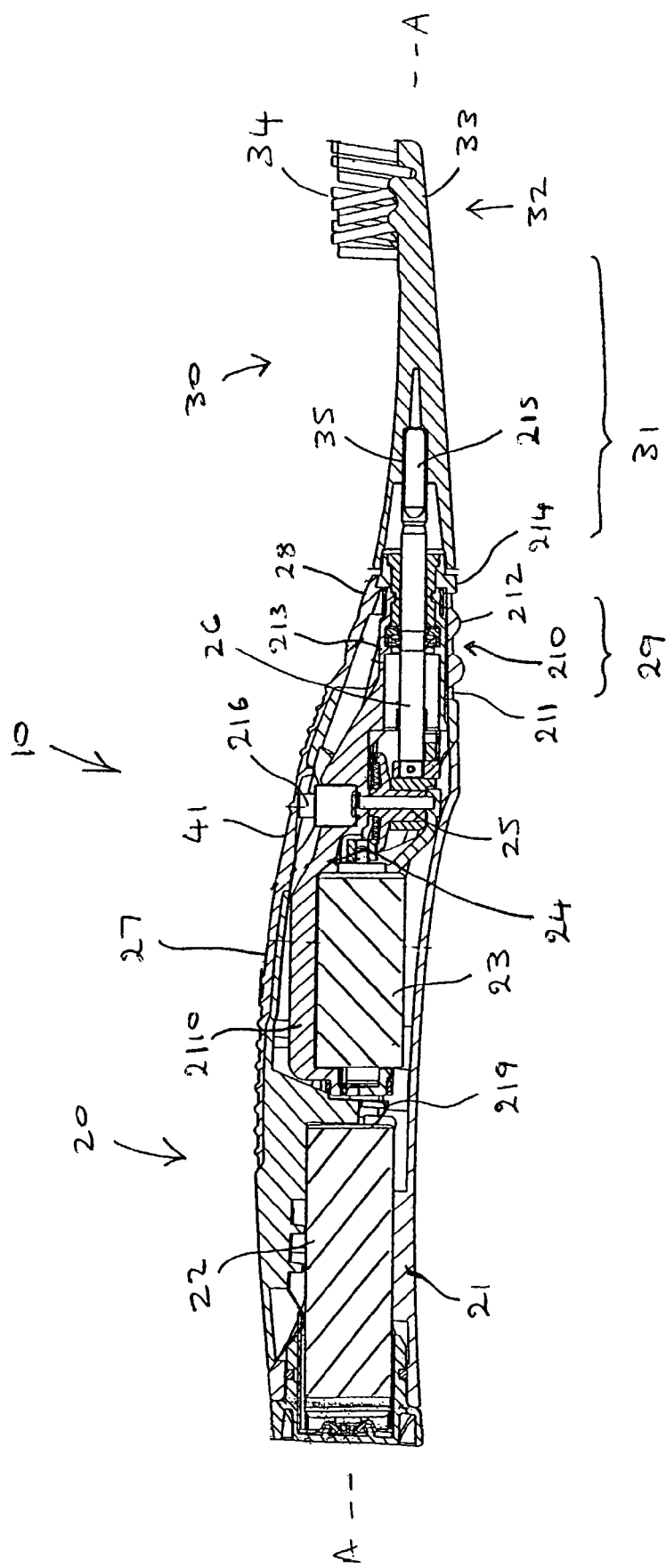
FIG. 6 shows a schematic overall longitudinal sectional view of another electric toothbrush of this invention.

FIG. 6 shows a more detailed cross section of an electric toothbrush according to the invention is shown, with parts corresponding to FIG. 1 numbered correspondingly (connections 217,218 are hidden). Motor 23 is rigidly connected to gear system 25 and sleeve 213 by means of a motor housing 2110 which is integrally extended to also house the gear system 25, and to form the sleeve 213. It is seen that the direction A-A follows a curved line. In the toothbrush of FIG. 6 the on-off switch 216 is enclosed within a flexible membrane 41 of the elastomeric material. The arrangement of bristles 34 is purely representative.

The invention claimed is:

1. An electrically powered toothbrush comprising:
   a handle which contains an electric motor and an electrical power supply,
   a head part connected to the handle to thereby define a longitudinal direction between the handle and the head part, the handle having longitudinally opposed ends, the head part incorporating an oral hygiene part to be driven in motion by the electric motor,
   a transmission means including a drive shaft between the electric motor and the oral hygiene part, the head part being flexibly and resiliently connected to the handle such that the head part can move resiliently under pressure of the oral hygiene part against a tooth surface,
   the electric motor being moveably mounted within the handle,
   wherein the head part and electric motor are connected together such that said movement of the head part under the pressure of the oral hygiene part against a tooth surface is communicated to the electric motor to cause the electric motor to move in response to said movement
   wherein the electric motor and transmission means are pivotally connected to the handle at a pivot point between the head part and the electric motor, the pivot point is provided by the handle having a resiliently flexible section, and the transmission means passes through the resiliently flexible section,
   wherein the resiliently flexible section is in two longitudinally disposed parts, a first part being relatively longitudinally further from the head part and a second part being relatively longitudinally closer to the head part,
   wherein the drive shaft passes through the second part of the handle in a direction toward the head part, with a resiliently flexible connection between the first and second parts, the resiliently flexible connection being provided by means of a composite plastic material-elastomer material section between the first and second part and which comprises a plastic material section between the first and second parts incorporating one or plural apertures in the plastic material and which apertures contain the elastomer material.

2. An electrically powered toothbrush according to claim 1 wherein the pivot point is located along the drive shaft between the electric motor and the head part.

3. An electrically powered toothbrush according to claim 1 wherein the transmission means includes a gearbox and the motor and transmission means are pivotally connected to the handle at a pivot point located along the drive shaft between the gear box and the head part.

4. An electrically powered toothbrush according to claim 1 wherein the pivot point allows the head part to move pivotally within the envelope of a cone with its apex at the pivot point, or about an arc centred on the pivot point.

5. An electrically powered toothbrush according to claim 1 wherein the one or plural apertures are in the form of elongate slots elongated in a direction transverse to the longitudinal direction.

6. An electrically powered toothbrush according to claim 1 wherein the handle comprises a shell made of a plastics material and enclosing internal components of the handle, and the drive shaft passes through the shell.

7. An electrically powered toothbrush according to claim 6 wherein the electric motor or the electric motor and transmission means are unsupported within the handle except at the point at which the drive shaft passes through the shell.

8. An electrically powered toothbrush according to claim 1 wherein a sleeve is provided having a bore through which the drive shaft passes, and the drive shaft passes through the resiliently flexible section via the sleeve.

9. An electrically powered toothbrush according to claim 8 wherein the sleeve is rigidly connected to the second part of the handle.

10. An electrically powered toothbrush according to claim 1 wherein the drive shaft comprises a stub shaft extending from the end of the handle closest to the head part, and to which a replaceable head part may be connected.

11. A toothbrush according to claim 1 wherein the transmission means transmits rotary motion to the head part to drive the oral hygiene part in rotary oral hygiene motion.

12. A toothbrush according to claim 1 wherein the transmission means transmits motion to the head part to drive the oral hygiene part in motion in which the oral hygiene part is moved both reciprocally longitudinally and also in oscillatory rotation about a rotation axis generally parallel to the longitudinal direction.

13. A handle for an electrically powered toothbrush, the handle being elongate along a longitudinal direction between longitudinally opposite ends, the handle comprising:

an electric motor and an electrical power supply, and having a connection at one end which is attachable to a toothbrush head part incorporating an oral hygiene part, a transmission means including a drive shaft connected to the electric motor and able to transmit motion from the electric motor to the head part when attached to thereby move the oral hygiene part in a suitable oral hygiene motion, wherein the electric motor is moveably mounted within the handle, the electric motor and transmission means being pivotally connected to the handle at a pivot point provided by the handle having a resiliently flexible section, the transmission means passing through this resiliently flexible section, wherein the resiliently flexible section is in two longitudinally disposed parts, a first part relatively longitudinally further from the connection and a second part relatively longitudinally closer to the connection, wherein the drive shaft passing through the second part of the handle, with a resiliently flexible connection between the first and second parts, the resiliently flexible connection being provided by means of a composite plastics material-elastomer material section between the first and second part and which comprises a plastics material section between the first and second parts incorporating one or plural apertures in the plastics material and which apertures contain the elastomer material.

\* \* \* \* \*